(12) United States Patent
Yin et al.

(10) Patent No.: US 11,197,829 B2
(45) Date of Patent: Dec. 14, 2021

(54) PREPARATION METHOD OF NALTREXONE IMPLANTS

(71) Applicant: Shenzhen ScienCare Medical Industries Co. Ltd., Shenzhen (CN)

(72) Inventors: Shugui Yin, Shenzhen (CN); Shiqiang Wang, Shenzhen (CN); Shaowei Jia, Shenzhen (CN); Tao Zhang, Shenzhen (CN); Qingzhe Liu, Shenzhen (CN)

(73) Assignee: Shenzhen ScienCare Medical Industries Co. Ltd., Shenzhen (CN)

( * ) Notice: Subject to any disclaimer, the term of this patent is extended or adjusted under 35 U.S.C. 154(b) by 361 days.

(21) Appl. No.: 16/137,546

(22) Filed: Sep. 21, 2018

(65) Prior Publication Data

US 2020/0060977 A1    Feb. 27, 2020

(30) Foreign Application Priority Data

Aug. 22, 2018 (CN) .......................... 201810961459.6

(51) Int. Cl.
| | | |
|---|---|---|
| *A61K 9/20* | (2006.01) | |
| *A61K 9/28* | (2006.01) | |
| *A61K 31/485* | (2006.01) | |
| *A61J 3/10* | (2006.01) | |
| *A61K 9/50* | (2006.01) | |

(52) U.S. Cl.
CPC .............. *A61K 9/2081* (2013.01); *A61J 3/10* (2013.01); *A61K 9/204* (2013.01); *A61K 9/2893* (2013.01); *A61K 9/5089* (2013.01); *A61K 31/485* (2013.01)

(58) Field of Classification Search
CPC .................................................... A61K 9/2893
See application file for complete search history.

(56) References Cited

U.S. PATENT DOCUMENTS

| | | | | |
|---|---|---|---|---|
| 2,799,241 A | * | 7/1957 | Wurster | |
| 3,896,762 A | * | 7/1975 | Banker | B05C 3/10 |
| | | | | 118/30 |
| 9,556,189 B2 | * | 1/2017 | Brittain | A61K 31/485 |
| 9,750,701 B2 | * | 9/2017 | Jans | A61K 9/20 |
| 10,588,822 B2 | * | 3/2020 | Zhu | A61J 3/00 |

FOREIGN PATENT DOCUMENTS

| | | | | |
|---|---|---|---|---|
| CN | 1973840 | | 6/2007 | |
| CN | 102512399 | | 6/2012 | |
| CN | 102512399 A | * | 5/2013 | ........... A61K 31/485 |

OTHER PUBLICATIONS

Parind M. Desai, Tablet coating by injection molding technology—Optimization of coating formulation attributes and coating process parameters, European Journal of Pharmaceutics and Biopharmaceutics 122 (2018) 25-36, publication date Oct. 9, 2017 (Year: 2017).*
CN102512399, Google English Translation, downloaded in Dec. 2020 (Year: 2020).*
Megha Agrawal, Application of Vacuum Drying in the Drug Processing and Drug Deliver Systems, Vacuum Technology & Coating, Aug. 2015 (Year: 2015).*
Jeremy M. Schieferstein, Hydrogel Microsphere Encapsulation Enhances the Flow Properties of Monoclonal Antibody Crystal Formulations, Adv. Therap. 2021 (Year: 2021).*
Milind Singh, Microsphere-Based Seamless Scaffolds Containing Macroscopic Gradients of Encapsulated Factors for Tissue Engineering, Tissue Eng Part C Methods. Dec. 2008; 14(4): 299-309 (Year: 2008).*

* cited by examiner

*Primary Examiner* — Mark V Stevens
*Assistant Examiner* — Alparslan Asan
(74) *Attorney, Agent, or Firm* — JCIPRNET

(57) ABSTRACT

The present invention relates to a technical field of pharmaceutical preparation, in particular to a preparation method of naltrexone implants, including the following steps: (1) dissolving naltrexone and polylactic acid in an organic solvent to form naltrexone microspheres, and drying; (2) placing the naltrexone microspheres in a heated tableting mold for tableting, and obtaining naltrexone implant tablets; (3) dissolving the polylactic acid in the organic solvent to obtain a coating solution, and placing the coating solution in a coating pool, and then immersing the naltrexone implant tablets in the coating solution, and drying in a suspended state.

10 Claims, 1 Drawing Sheet

PREPARATION METHOD OF NALTREXONE IMPLANTS

CROSS-REFERENCE TO RELATED APPLICATION

This application claims the priority benefit of China application serial no. 201810961459.6, filed on Aug. 22, 2018. The entirety of the above-mentioned patent application is hereby incorporated by reference herein and made a part of this specification.

BACKGROUND

Technical Field

The present invention relates to the technical field of pharmaceutical preparation, in particular to a preparation method of naltrexone implants.

Description of Related Art

Drugs, such as heroin, and alcohol abuse are global public nuisances. In recent years, it has re-spread in China and increased year by year. For the detoxification treatment of addicts, the relapse rate is as high as 90-95% regardless of the method. In order to reduce the relapse rate, two measures, which are completely opposite in pharmacology, are often used internationally, one is to maintain treatment with an opioid receptor agonist such as methadone or LAAM; the other is to use opioid receptor antagonists such as naltrexone. The former is essentially a palliative measure aimed at substitution, while the latter program reflects the positive efforts of biomedical methods to prevent relapse.

Naltrexone, 17-cyclopropylmethyl-4,5α-epoxy-3,14 di-light morphinan-6-one, is a potent block of exogenous opioids. Naltrexone was first synthesized in 1965, and tests from the 1970s to the early 1980s showed that naltrexone can prevent relapse by eliminating drug cravings and drug-seeking behavior. In 1984, naltrexone was approved by the SFDA for anti-relapse therapy for opioid addicts. In 1995, China succeeded in imitation of naltrexone by the Institute of Pharmacology and Toxicology of the Academy of Military Medical Sciences. The approved dosage is naltrexone hydrochloride tablets. Although naltrexone is well absorbed orally, it is susceptible to first-pass effects, and its oral bioavailability is only 5%-40%. The activity of naltrexone is produced by its parent structure and 6-β-naltrexol metabolites, which are mainly excreted by the kidneys (53% to 79% of the dose). And the average elimination half-lives of naltrexone and 6-β-naltrexol are 4 hours and 13 hours, respectively. It is reported that most patients who rely heavily on opioid often forget or deliberately choose not to take their medicine and the treatment become ineffective to overcome the dependence.

Therefore, in order to circumvent the above problems, the development of a long-acting, sustained-release preparation has apparent clinical significance. Lance L Gooberman first reported the naltrexone implantable tablets in WO1998030171. In these tablets, naltrexone is embedded in magnesium stearate complex, which can release the naltrexone in 5-6 weeks. "Prodetoxone pellets" listed in Russia is also a naltrexone implant which gives effective opioid blockage for 12 to 14 weeks. Another version of implants of naltrexone has been developed by Dr. George O'Neill of GO-Medical Industries which includes naltrexone embedded in a matrix of biodegradable polymer microspheres. These implants have been reported to release naltrexone for 5-12 months or more.

Patent CN102512399A discloses a long-acting naltrexone implant including sustained release microspheres made of polylactic acid and naltrexone, which are formed into a final implant by tableting and coating. Patent CN 1973840 A also discloses a long-acting sustained-release preparation for detoxification, which is also prepared by tableting and coating the sustained release microspheres made of polylactic acid and naltrexone. However, in the above prior art, the preparation process of the naltrexone implant has many defects, for instance, the naltrexone microspheres are easy to rupture during tableting process, resulting in the release of naltrexone in the body. Another case in point is that the integrity of the capsule is difficult to control, which also affects the sustained release of the final product. At present, most of the marketed naltrexone implants only can be detected in the blood after 24 hours since the implantation, which indicates the drug works slowly.

SUMMARY

Based on the drawbacks of the prior art, the present invention provides a preparation method of naltrexone implants. In the present invention, mixing a certain amount of naltrexone crystals with the naltrexone microspheres in the tableting process, and controlling a certain tableting temperature to form a skeleton supporting structure fusing with naltrexone microspheres, which can avoid rupture of the naltrexone microspheres during tableting and ensure uniform distribution of drugs in the implant; Furthermore, a special coating device and a suspended drying method are used in the coating process to prevent the coat from being broken due to adhesion between the tablets.

The present invention provides a preparation method of naltrexone implants, including the following steps:

(1) preparing naltrexone microspheres: dissolving naltrexone and polylactic acid in an organic solvent to form microspheres, and drying;

(2) tableting: placing naltrexone microspheres in a heated tableting mold for tableting, and obtaining naltrexone implant tablets;

(3) coating: dissolving polylactic acid in an organic solvent to obtain the coating solution, and placing the solution in a coating pool, and then immersing the naltrexone implant tablets in the coating solution, and drying in the suspended state.

Preferably, in step (1) and (3), the polylactic acid are the same, both of them are selected from one or more of L-polylactic acid, D-polylactic acid, DL-polylactic acid, and polylactide glycolide.

More preferably, in step (1) and (3), the polylactic acid is DL-polylactic acid.

More preferably, in step (1) and (3), the molecular weight of the polylactic acid is 50,000-90,000, wherein in step (1), the concentration of the solution made by naltrexone and polylactic acid dissolved in an organic solvent is 15-25%; and the concentration of the coating solution in the step (3) is 5-9%.

Preferably, in step (1), the mass ratio of naltrexone to polylactic acid is 0.5-1.8:1.

More preferably, in step (1), the mass ratio of naltrexone to polylactic acid is 0.8-1.5:1.

Preferably, in step (1), the organic solvent is dichloromethane and/or ethyl acetate.

Preferably, in step (1), dissolving naltrexone and polylactic acid in an organic solvent, and stirring at 35 to 40° C. to form microspheres.

Preferably, in step (1), the diameter of naltrexone microspheres obtained is 50 to 300 μm.

Preferably, in step (2), mixing the naltrexone microspheres with the naltrexone crystals before tableting, and then tableting them in a heated tableting mold.

Preferably, preparing the naltrexone crystals with a conventional method or as follows: dissolving the naltrexone hydrochloride in water, mixing with $NaHCO_3$ solution, and extracting with dichloromethane for 3-4 times, and then concentrating and drying the extract.

More preferably, dissolving the naltrexone hydrochloride in 15-20 volumes of water, and mixing with an equal volume of $NaHCO_3$ solution.

More preferably, the concentration of $NaHCO_3$ solution is 3-4%.

Preferably, the naltrexone crystal has a length of 5 to 50 μm.

More preferably, the naltrexone crystal has a length of 10 to 30 μm.

Preferably, mixing the naltrexone microspheres and naltrexone crystals at a mass ratio of 100:10-20.

More preferably, mixing the naltrexone microspheres and naltrexone crystals at a mass ratio of 100:12-15.

Preferably, in step (2), heating the tableting mold to 35-50° C.

More preferably, in step (2), heating the tableting mold to 37-40° C.

Preferably, in step (2), the pressure of the tableting is 8-15 KN.

More preferably, in step (2), the pressure of the tableting is 11-13 KN.

Preferably, in the step (3), setting a liquid tube with small holes inside the coating pool, and immersing the liquid tube in the coating solution.

More preferably, the density of small holes on liquid tube is at least 100/30 cm tube length and the diameter of the small holes is 1.5-2.5 mm, which makes the coating solution easy to enter the liquid tube to coat the implants.

Preferably, in step (3), coating the naltrexone implants by moving them from one end of the liquid tube to the other with an external driving force.

More preferably, the diameter of the inlet of the liquid tube is 0.5-1.5 mm larger than the outlet, and the diameter of the outlet of the liquid tube is 1.5-2 mm larger than the diameter of the naltrexone implant.

More preferably, the diameter of the inlet of the liquid tube is 0.8-1.2 mm larger than the outlet, and the diameter of the outlet of the liquid tube is 1.5-1.8 mm larger than the diameter of the naltrexone implant.

More preferably, the diameter of the inlet of the liquid tube is 0.9 mm larger than the outlet, and the diameter of the outlet of the liquid tube is 1.5 mm larger than the diameter of the naltrexone implant.

Preferably, in step (3), the coating time of naltrexone implants passing through the liquid tube is 15-50 s.

More preferably, in step (3), the coating time of naltrexone implants passing through the liquid tube is 30 s.

Preferably, in step (3), the coating temperature is 33-40° C.

More preferably, in step (3), the coating temperature is 37° C.

Preferably, in step (3), the suspended drying temperature is 18-24° C.

More preferably, in step (3), the suspended drying temperature is 20° C.

Preferably, in step (3), the suspended drying time is 15-45s.

More preferably, in step (3), the suspended drying time is 30s.

More preferably, in step (3), after drying in the suspended state, continuing to dry under vacuum at 30-50° C. for 48-50 h.

The present invention also provides a naltrexone implant prepared by the above preparation method.

The advantages of the present invention are as follows:

(1) In tableting process, appropriate amount of naltrexone crystals is added to well mix with the naltrexone microspheres to form a skeleton structure, thereby avoiding rupture of the naltrexone microspheres, which leads to uneven distribution of the drug in the implants, and sudden release in the body.

(2) Reasonable Controlling the tableting temperature, so that the naltrexone microspheres and naltrexone crystals can be slightly melted and joined together to support the tablets from the inside, which can prevent the liquid from penetrating into the microspheres, and avoid the collapse of microspheres and the drug burst release, thereby greatly improve the yield of the product.

(3) In the present invention, the tableting process is without cleaning the microspheres to avoid the loss of naltrexone. However, residues such as organic solvents are guaranteed to ensure the safety of the drug; Furthermore, the tableting makes the volume of the implants smaller, ensuring a higher drug content in the implants within a certain volume, which significantly improve the pharmacodynamics effect.

(4) The liquid tube and suspension dryer are used in the present invention, so that the PLA with higher viscosity can be uniformly wrapped on the surface of the naltrexone implants, thereby effectively avoiding the incomplete coating caused by the adhesion between each other. Simultaneously, the coating temperature and time have a great influence on the quality of the coating. Due to the large viscosity of the PLA, it is difficult to form a uniform coat on the surface of the implants. Strictly controlling the temperature and time of the coating process helps to form thin coat, and the integrity of the coating in the present invention is more than 99%.

(5) The molecular weight of the polylactic acid is 50,000-90,000, which has a great influence on the release degree of the implants after the coating. On the one hand, too small molecular weight will result in too fast release; and on the other hand, excessive molecular weight can cause the drug to be difficult to release, the drug can be detected in the blood at least 2-3 days after implantation in the body, and the release rate cannot reach the lowest therapeutic dose, leading to the poor therapeutic effect.

DESCRIPTION OF THE EMBODIMENTS

Example 1 Preparation Method of Naltrexone Implants

The preparation steps are as follows:

(1) Preparing naltrexone microspheres: dissolving the naltrexone and polylactic acid (molecular weight is 60,000) with a mass ratio of 1:1 in methylene chloride, and the concentration of the obtained solution is 20%; stirring at 37° C. to form microspheres suspended in solution, then filtering, and vacuum drying the microspheres.

Wherein, the microspheres have a diameter of 50 to 200 µm.

(2) Preparing naltrexone crystal: dissolving naltrexone hydrochloride in 20 times volume of water, and then mixing it with an equal volume of 3% $NaHCO_3$ solution, extracting with dichloromethane for 3 times, and then concentrating and vacuum drying the extract, and finally obtaining the naltrexone crystal.

Wherein, the naltrexone crystal has a length of 10 to 30 µm.

(3) Tableting: mixing the naltrexone microspheres of step (1) and the naltrexone crystal of step (2) at a mass ratio of 100:10 to obtain the mixture of naltrexone microspheres, shocking while mixing, so that the crystal can uniformly distribute in the microspheres and form a dendritic shape; heating the tableting mold to 40° C., and tableting the mixture of naltrexone microspheres at a pressure of 13 KN to obtain a naltrexone implant tablet.

Figure 1:
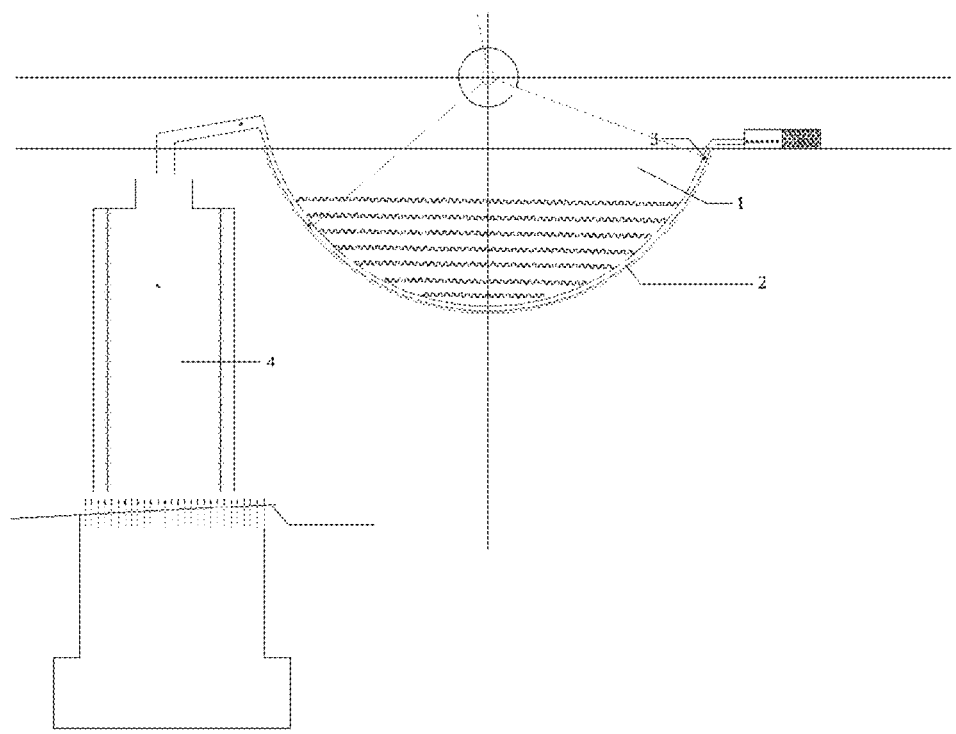
FIG. 1 is a sketch map of the coating pool and drying apparatus used in the coating process.

(4) Coating: as shown in FIG. 1, dissolving the DL-polylactic acid with a molecular weight of 60,000 in dichloromethane to form a 6% coating solution, placing the solution in the coating pool 1, pushing the naltrexone implants 3 to the liquid tube 2 which is disposed inside the coating pool 1 and uniformly distributed with small holes, pushing the implants 3 from one end of the liquid tube 2 to the other end by an external force to coat the tablets; the coating time is 30 s, and the coating temperature is 37° C.; transferring the coated naltrexone implants to a suspension dryer 4, drying at 20° C. for 30 s, and then drying under vacuum at 40° C. for 48 h.

In step (4), the density of small holes on the liquid tube 2 is 150/30 cm, the diameter from the inlet to the outlet of the liquid tube 2 is gradually reduced, and the inlet is 0.9 mm larger than the outlet; the diameter of the outlet of the liquid tube 2 is 1.5 mm larger than the diameter of the naltrexone implant 3.

Example 2 Preparation Method of Naltrexone Implants (1) Preparing naltrexone microspheres: dissolving the naltrexone and polylactic acid (molecular weight is 50,000) with a mass ratio of 0.6:1 in methylene chloride, and the concentration of the obtained solution is 20%; stirring at 35° C. to form microspheres suspended in solution, then filtering, and vacuum drying the microspheres.

Wherein, the microspheres have a diameter of 50 to 180 µm.

(2) Preparing naltrexone crystal: dissolving naltrexone hydrochloride in 16 times volume of water, and then mixing it with an equal volume of 4% $NaHCO_3$ solution, extracting with dichloromethane for 3 times, and then concentrating and vacuum drying the extract, and finally obtaining the naltrexone crystal.

Wherein, the naltrexone crystal has a length of 5 to 20 µm.

(3) Tableting: mixing the naltrexone microspheres of step (1) and the naltrexone crystal of step (2) at a mass ratio of 100:15 to obtain the mixture of naltrexone microspheres, shocking while mixing, so that the crystal can uniformly distribute in the microspheres and form a dendritic shape; heating the tableting mold to 37° C., and tableting the mixture of naltrexone microspheres at a pressure of 11 KN to obtain a naltrexone implant tablet.

(4) Coating: as shown in FIG. 1, dissolving the DL-polylactic acid with a molecular weight of 50,000 in dichloromethane to form a 6% coating solution, placing the solution in the coating pool 1, pushing the naltrexone implants 3 to the liquid tube 2 which is disposed inside the coating pool 1 and uniformly distributed with small holes, pushing the implants 3 from one end of the liquid tube 2 to the other end by an external force to coat the tablets; the coating time is 50 s, and the coating temperature is 33° C.; transferring the coated naltrexone implants to a suspension dryer 4, drying at 24° C. for 15 s, and then drying under vacuum at 30° C. for 50 h.

In step (4), the density of small holes on the liquid tube 2 is 100/30 cm, the diameter from the inlet to the outlet of the liquid tube 2 is gradually reduced; the diameter of the outlet of the liquid tube 2 is 1.5 mm larger than the diameter of the naltrexone implant 3.

Example 3 Preparation Method of Naltrexone Implants (1) Preparing naltrexone microspheres: dissolving the naltrexone and polylactic acid (molecular weight is 70,000) with a mass ratio of 0.8:1 in methylene chloride, and the concentration of the obtained solution is 18%; stirring at 36° C. to form microspheres, which is suspended in solution, then filtering, and vacuum drying the microspheres.

Wherein, the microspheres have a diameter of 50 to 200 µm.

(2) Preparing naltrexone crystal: dissolving naltrexone hydrochloride in 18 times volume of water, and then mixing it with an equal volume of 3% $NaHCO_3$ solution, extracting with dichloromethane for 3 times, and then concentrating and vacuum drying the extract, and finally obtaining the naltrexone crystal.

Wherein, the naltrexone crystal has a length of 30 to 50 µm.

(3) Tableting: mixing the naltrexone microspheres of step (1) and the naltrexone crystal of step (2) at a mass ratio of 100:14 to obtain the mixture of naltrexone microspheres, shocking while mixing, so that the crystal can uniformly distribute in the microspheres and form a dendritic shape; heating the tableting mold to 38° C., and tableting the mixture of naltrexone microspheres at a pressure of 15 KN to obtain a naltrexone implant tablet.

(4) Coating: as shown in FIG. 1, dissolving the DL-polylactic acid with a molecular weight of 70,000 in dichloromethane to foci n a 7% coating solution, placing the solution in the coating pool 1, pushing the naltrexone implants 3 to the liquid tube 2 which is disposed inside the coating pool 1 and uniformly distributed with small holes, pushing the implants 3 from one end of the liquid tube 2 to the other end by an external force to coat the tablets; the coating time is 5 s, and the coating temperature is 40° C.; transferring the coated naltrexone implants to a suspension dryer 4, drying at 18° C. for 45 s, and then drying under vacuum at 50° C. for 50 h.

In step (4), the density of small holes on the liquid tube 2 is 250/30 cm, the diameter at the inlet of the liquid tube 2 is 0.8 mm larger than the outlet; the diameter of the outlet of the liquid tube 2 is 1.8 mm larger than the diameter of the naltrexone implant 3.

Example 4 Preparation Method of Naltrexone Implants (1) Dissolving the naltrexone and polylactic acid (molecular weight is 70,000) with a mass ratio of 1.5:1 in methylene chloride, and the concentration of the obtained solution is 25%; stirring at 40° C. to form microspheres suspended in solution, then filtering, and vacuum drying the microspheres.

Wherein, the microspheres have a diameter of 80 to 250 μm.

(2) Dissolving naltrexone hydrochloride in 17 times volume of water, and then mixing it with an equal volume of 3.2% NaHCO$_3$ solution, extracting with dichloromethane for 4 times, and then concentrating and vacuum drying the extract, and finally obtaining the naltrexone crystal.

Wherein, the naltrexone crystal has a length of 2 to 15 μm.

(3) Tableting: mixing the naltrexone microspheres of step (1) and the naltrexone crystal of step (2) at a mass ratio of 100:10 to obtain the mixture of naltrexone microspheres, shocking while mixing, so that the crystal can uniformly distribute in the microspheres and form a dendritic shape; heating the tableting mold to 35° C., and tableting the mixture of naltrexone microspheres at a pressure of 8 KN to obtain a naltrexone implant tablet.

(4) Coating: as shown in FIG. 1, dissolving the DL-polylactic acid with a molecular weight of 90,000 in dichloromethane to form a 9% coating solution, placing the solution in the coating pool 1, pushing the naltrexone implants 3 to the liquid tube 2 which is disposed inside the coating pool 1 and uniformly distributed with small holes, pushing the implants 3 from one end of the liquid tube 2 to the other end by an external force to coat the tablets; the coating time is 35 s, and the coating temperature is 38° C.; transferring the coated naltrexone implants to a suspension dryer 4, drying at 25° C. for 35 s, and then drying under vacuum at 34° C. for 48 h.

In step (4), the density of small holes on the liquid tube 2 is 200/30 cm, the diameter from the inlet to the outlet of the liquid tube 2 is gradually reduced, and the inlet is 1.2 mm larger than the outlet; the diameter of the outlet of the liquid tube 2 is 1.8 mm larger than the diameter of the naltrexone implant 3.

Example 5 Preparation Method of Naltrexone Implants (1) Dissolving the naltrexone and polylactic acid (molecular weight is 80,000) with a mass ratio of 1.8:1 in methylene chloride, and the concentration of the obtained solution is 22%; stirring at 37° C. to form microspheres suspended in solution, then filtering, and vacuum drying the microspheres.

Wherein, the microspheres have a diameter of 80 to 200 μm.

(2) Dissolving naltrexone hydrochloride in 15 times volume of water, and then mixing it with an equal volume of 4% NaHCO$_3$ solution, extracting with dichloromethane for 3 times, and then concentrating and vacuum drying the extract, and finally obtaining the naltrexone crystal.

Wherein, the naltrexone crystal has a length of 10 to 70 μm.

(3) Tableting: mixing the naltrexone microspheres of step (1) and the naltrexone crystal of step (2) at a mass ratio of 100:10 to obtain the mixture of naltrexone microspheres, shocking while mixing, so that the crystal can uniformly distribute in the microspheres and form a dendritic shape; heating the tableting mold to 42° C., and tableting the mixture of naltrexone microspheres at a pressure of 14 KN to obtain a naltrexone implant tablet.

(4) Coating: as shown in FIG. 1, dissolving the DL-polylactic acid with a molecular weight of 80,000 in dichloromethane to faun a 8% coating solution, placing the solution in the coating pool 1, pushing the naltrexone implants 3 to the liquid tube 2 which is disposed inside the coating pool 1 and uniformly distributed with small holes, pushing the implants 3 from one end of the liquid tube 2 to the other end by an external force to coat the tablets; the coating time is 40 s, and the coating temperature is 36° C.; transferring the coated naltrexone implants to a suspension dryer 4, drying at 23° C. for 40 s, and then drying under vacuum at 48° C. for 49 h.

In step (4), the density of small holes on the liquid tube 2 is 300/30 cm, the diameter at the inlet of the liquid tube 2 is 1.5 mm larger than the outlet; the diameter of the outlet of the liquid tube 2 is 2 mm larger than the diameter of the naltrexone implant 3.

Example 6 Preparation Method of Naltrexone Implants (1) Dissolving the naltrexone and polylactic acid (molecular weight is 60,000) with a mass ratio of 1:1 in methylene chloride, and the concentration of the obtained solution is 20%; stirring at 37° C. to form microspheres suspended in solution, then filtering, and vacuum drying microspheres.

Wherein, the microspheres have a diameter of 50 to 200 μm.

(2) Tableting: heating the tableting mold to 40° C., and tableting the naltrexone microspheres at a pressure of 13 KN to obtain a naltrexone implant tablet.

(4) Coating: as shown in FIG. 1, dissolving the DL-polylactic acid with a molecular weight of 60,000 in dichloromethane to form a 6% coating solution, placing the solution in the coating pool 1, pushing the naltrexone implants 3 to the liquid tube 2 which is disposed inside the coating pool 1 and uniformly distributed with small holes, pushing the implants 3 from one end of the liquid tube 2 to the other end by an external force to coat the tablets; the coating time is 30 s, and the coating temperature is 37° C.; transferring the coated naltrexone implants to a suspension dryer 4, drying at 20° C. for 30 s, and then drying under vacuum at 40° C. for 48 h.

In step (4), the density of small holes on the liquid tube 2 is 150/30 cm, the diameter from the inlet to the outlet of the liquid tube 2 is gradually reduced, and the inlet is 0.9 mm larger than the outlet; the diameter of the outlet of the liquid tube 2 is 1.5 mm larger than the diameter of the naltrexone implant 3.

Contrast Example 1 Preparation Method of Naltrexone Implants

Except that the tableting temperature is 50° C. in step (3), the other steps are the same as Example 1.

Contrast Example 2 Preparation Method of Naltrexone Implants

Except that the microsphere is washed, the other steps are the same as Example 1, the prepare steps are as follows:

(1) Preparing naltrexone microspheres: dissolving the naltrexone and polylactic acid (molecular weight is 60,000) with a mass ratio of 1:1 in methylene chloride, and the concentration of the obtained solution is 20%; stirring at 37° C. to form microspheres suspended in solution, then filtering, washing with distilled water and vacuum drying the microspheres.

Wherein, the microspheres have a diameter of 50 to 200 μm.

(2) Preparing naltrexone crystal: dissolving naltrexone hydrochloride in 20 times volume of water, and then mixing it with an equal volume of 3% $NaHCO_3$ solution, extracting with dichloromethane for 3 times, and then concentrating and vacuum drying the extract, and finally obtaining the naltrexone crystal.

Wherein, the naltrexone crystal has a length of 10 to 30 μm.

(3) Tableting: mixing the naltrexone microspheres of step (1) and the naltrexone crystal of step (2) at a mass ratio of 100:10 to obtain the mixture of naltrexone microspheres, shocking while mixing, so that the crystal can uniformly distribute in the microspheres and form a dendritic shape; heating the tableting mold to 40° C., and tableting the mixture of naltrexone microspheres at a pressure of 13 KN to obtain a naltrexone implant tablet.

(4) Coating: as shown in FIG. 1, dissolving the DL-polylactic acid with a molecular weight of 60,000 in dichloromethane to form a 6% coating solution, placing the solution in the coating pool 1, pushing the naltrexone implants 3 to the liquid tube 2 which is disposed inside the coating pool 1 and uniformly distributed with small holes, pushing the implants 3 from one end of the liquid tube 2 to the other end by an external force to coat the tablets; the coating time is 30 s, and the coating temperature is 37° C.; transferring the coated naltrexone implants to a suspension dryer 4, drying at 20° C. for 30 s, and then drying under vacuum at 40° C. for 48 h.

In step (4), the density of small holes on the liquid tube 2 is 150/30 cm, the diameter from the inlet to the outlet of the liquid tube 2 is gradually reduced, and the inlet is 0.9 mm larger than the outlet; the diameter of the outlet of the liquid tube 2 is 1.5 mm larger than the diameter of the naltrexone implant 3.

Contrast Example 3 Preparation Method of Naltrexone Implants

Except that the immersing time for the naltrexone implants to coat is 50 s, the other steps are the same as Example 1.

Contrast Example 4 Preparation Method of Naltrexone Implants

Except that the coating time of the naltrexone implants is 45° C., the other steps are the same as Example 1.

Contrast Example 5 Preparation Method of Naltrexone Implants

Except that the molecule weight of the naltrexone implant is 40,000, the other steps are the same as Example 1.

Contrast Example 6 Preparation Method of Naltrexone Implants

Except that the mass ratio of naltrexone microspheres to naltrexone crystals is 100:5, the other steps are the same as Example 1.

Test Example 1 the Drug Content, Yield and Coating Thickness of Naltrexone Implants Prepared by the Above Methods Determining the drug content of the implants prepared in Examples 1-6 and Contrast Examples 1-6 according to the quality standard of naltrexone implants with the method of HPLC.

At the same time, counting the number of finished products and defective products prepared by each process, and calculating the yield.

TABLE 1

The drug content and yield of implants prepared by the different methods

| Groups | Drug Content (%) | Yield (%) | Coating Thickness (mm) |
| --- | --- | --- | --- |
| Example 1 | 49.1 | 94 | 0.0023 ± 0.0003 |
| Example 2 | 45.5 | 96 | 0.0025 ± 0.0001 |
| Example 3 | 52.7 | 93 | 0.0028 ± 0.0003 |
| Example 4 | 45.6 | 95 | 0.0020 ± 0.0004 |
| Example 5 | 54.5 | 92 | 0.0029 ± 0.0004 |
| Example 6 | 39.1 | 80 | 0.0022 ± 0.0004 |
| Contrast Example 1 | 38.5 | 53 | 0.0032 ± 0.0008 |
| Contrast Example 2 | 26.7 | 72 | 0.0030 ± 0.0012 |
| Contrast Example 3 | 38.8 | 72 | 0.010 ± 0.007 |
| Contrast Example 4 | 39.7 | 71 | 0.0012 ± 0.010 |
| Contrast Example 5 | 38.7 | 73 | 0.009 ± 0.017 |
| Contrast Example 6 | 42.3 | 83 | 0.0031 ± 0.006 |

Figure 2:
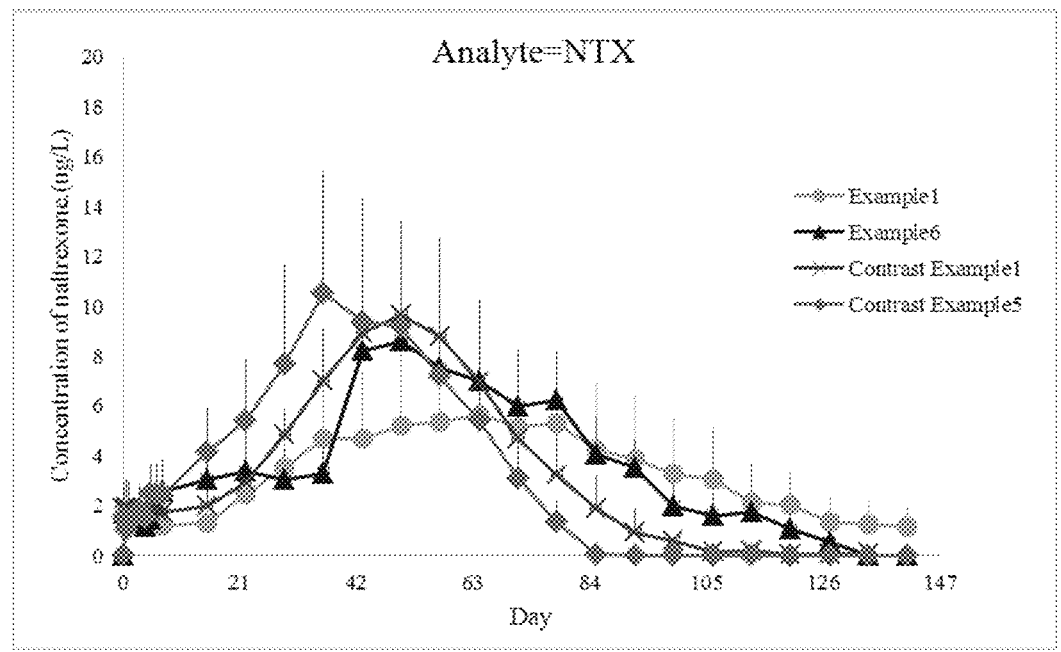
FIG. 2 is the mean blood concentration-time curve of naltrexone in the plasma of the subjects after subcutaneous implantation of naltrexone implants in Test Example 2.

Test Example 2 Clinical Results of Naltrexone Implants Prepared by Different Methods Subcutaneously implanting 10 tablets of the naltrexone implants prepared in Example 1, Example 6, Comparative Example 1 and Comparative Example 5 into the patients respectively. Determining the blood concentration after implantation and the results are shown in FIG. 2.

The results show that the naltrexone implant tableting method of the present invention can effectively improve the sustained release of the drug and avoid the burst release due to collapse of the microspheres.

The detailed description is intended to illustrate one of the preferred embodiments of the present invention. These examples are non-limiting and should not be construed as limiting any aspect of invention. It should be noted that any modification and equivalent replacement within the spirit and principle of the invention should be included in the protection scope of the invention.

What is claimed is:

1. A preparation method of naltrexone implants, comprising the following steps:
    (1) preparing naltrexone microspheres: dissolving naltrexone and polylactic acid in a first organic solvent to form the naltrexone microspheres, and drying;
    (2) tableting: placing the naltrexone microspheres in a heated tableting mold for tableting, and obtaining naltrexone implant tablets;
    (3) coating: dissolving the polylactic acid in a second organic solvent to obtain a coating solution, and placing the coating solution in a coating pool, and then immersing the naltrexone implant tablets in the coating solution, and drying in a suspended state,
    wherein, in step (2), adding and mixing naltrexone crystals with the naltrexone microspheres before tableting, and then tableting in the heated tableting mold to obtain the naltrexone implant tablets, wherein, in step (3), setting a tube inside the coating pool, and immersing the tube in the coating solution before immersing the naltrexone implant tablets in the coating solution, and then pushing the naltrexone implant tablets through the tube which is disposed inside the coating pool and uniformly distributed with small holes, wherein the density of small holes on the tube is at least 100/30 cm tube length, the tube comprising small holes, an inlet, a body and an outlet, the body connects the inlet and the outlet, and the small holes, the inlet, the body and the outlet of the tube are immersed in the coating solution of the coating pool, wherein the coating time of the naltrexone implant tablets passing through a tube is 15-50 s, and the coating temperature is 33-40° C.

2. The preparation method of naltrexone implants of claim 1, wherein, in step (2), a mass ratio of the naltrexone microspheres to the naltrexone crystals is 100:10-20.

3. The preparation method of naltrexone implants of claim 1, wherein, in step (2), a mass ratio of the naltrexone microspheres to the naltrexone crystals is 100:12-15.

4. The preparation method of naltrexone implants of claim 1, wherein, in step (2), heating the tableting mold to 35-50° C.

5. The preparation method of naltrexone implants of claim 1, wherein, in step (2), heating the tableting mold to 37-40° C.

6. The preparation method of naltrexone implants of claim 1, wherein, in step (3), coating the naltrexone implant tablets by moving them from one end of the tube to the other end with an external driving force.

7. The preparation method of naltrexone implants of claim 1, wherein, the diameter of the inlet of the tube is 0.5-1.5 mm larger than the diameter of the outlet, and the diameter of the outlet of the tube is 1.5-2 mm larger than the diameter of the naltrexone implant tablets.

8. The preparation method of naltrexone implants of claim 1, wherein, the diameter of the inlet of the tube is 0.8-1.2 mm larger than the diameter of the outlet, and the diameter of the outlet of the tube is 1.5-1.8 mm larger than the diameter of the naltrexone implant tablets.

9. The preparation method of naltrexone implants of claim 1, wherein the coating time of the naltrexone implant tablets passing through a tube is 30 s, and the coating temperature is 37° C.

10. The preparation method of naltrexone implants of claim 1, wherein, in step (3), after drying in the suspended state at 18-24° C. for 15-45s, continuing to dry under vacuum at 30-50° C. for 48-50 h.

* * * * *